US011116992B2

(12) United States Patent
Shilton

(10) Patent No.: US 11,116,992 B2
(45) Date of Patent: Sep. 14, 2021

(54) GAMMA RADIATION SOURCE COMPRISING LOW-DENSITY DEFORMABLE/COMPRESSIBLE IRIDIUM ALLOY AND AN ENCAPSULATION

(71) Applicant: QSA GLOBAL INC., Burlington, MA (US)

(72) Inventor: Mark Shilton, Chelmsford, MA (US)

(73) Assignee: QSA GLOBAL, INC., Burlington, MA (US)

( * ) Notice: Subject to any disclaimer, the term of this patent is extended or adjusted under 35 U.S.C. 154(b) by 224 days.

(21) Appl. No.: 16/444,371

(22) Filed: Jun. 18, 2019

(65) Prior Publication Data

US 2020/0027621 A1  Jan. 23, 2020

Related U.S. Application Data

(60) Provisional application No. 62/686,748, filed on Jun. 19, 2018.

(51) Int. Cl.
*A61N 5/10* (2006.01)
*A61B 6/00* (2006.01)
*G21G 4/08* (2006.01)

(52) U.S. Cl.
CPC .............. *A61N 5/1001* (2013.01); *A61B 6/40* (2013.01); *A61N 5/10* (2013.01); *G21G 4/08* (2013.01); *A61N 2005/1019* (2013.01); *A61N 2005/1022* (2013.01); *A61N 2005/1023* (2013.01); *A61N 2005/1024* (2013.01)

(58) Field of Classification Search
CPC .......... A61B 6/40; A61N 5/10; A61N 5/1001; A61N 2005/1019; A61N 2005/1022; A61N 2005/1023; A61N 2005/1024
USPC ..................................... 378/64, 65, 119, 120
See application file for complete search history.

(56) References Cited

U.S. PATENT DOCUMENTS

| | | | |
|---|---|---|---|
| 4,406,693 A | | 9/1983 | Heshmatpour et al. |
| 5,840,008 A | * | 11/1998 | Klein .................... A61N 5/1002 600/3 |
| 6,099,458 A | * | 8/2000 | Robertson ............ A61N 5/1027 600/3 |
| 6,132,359 A | * | 10/2000 | Bolenbaugh ......... A61N 5/1027 600/8 |
| 6,248,057 B1 | * | 6/2001 | Mavity ................ A61N 5/1027 600/3 |
| 6,547,816 B1 | * | 4/2003 | O'Foghludha ....... A61N 5/1001 600/3 |
| 6,554,756 B1 | * | 4/2003 | Schaart .............. A61K 51/1282 600/3 |
| 6,689,043 B1 | * | 2/2004 | McIntire .............. A61N 5/1027 424/1.29 |
| 6,716,156 B2 | * | 4/2004 | Menuhr ............... A61N 5/1027 600/8 |

(Continued)

FOREIGN PATENT DOCUMENTS

WO PCT/US2015/029806  5/2015
WO  2015105539  7/2015

(Continued)

OTHER PUBLICATIONS

Takashi Yamaoka, "Antiferromagnetism in γ-Phase Mn—Ir Alloys" Journal of the Physical Society of Japan, 1974, pp. 445-450.

(Continued)

*Primary Examiner* — Allen C. Ho
(74) *Attorney, Agent, or Firm* — McCarter & English, LLP

(57) ABSTRACT

The disclosure pertains to improvements in a gamma radiation source, typically containing low-density alloys or compounds or composites of iridium in mechanically deformable and compressible configurations, within a sealed encapsulation, and methods of manufacture thereof.

20 Claims, 5 Drawing Sheets

(56) References Cited

U.S. PATENT DOCUMENTS

| | | | | |
|---|---|---|---|---|
| 7,311,655 | B2* | 12/2007 | Schaart | A61K 51/1282 |
| | | | | 252/625 |
| 8,357,316 | B2* | 1/2013 | Munro, III | C01B 33/00 |
| | | | | 252/645 |
| 9,165,692 | B2* | 10/2015 | Finger | G21G 4/00 |
| 10,141,080 | B2* | 11/2018 | Vose | G21G 4/00 |
| 10,607,743 | B2* | 3/2020 | Vose | G21G 4/06 |
| 10,714,226 | B2* | 7/2020 | Vose | A61N 5/1001 |
| 10,811,156 | B2* | 10/2020 | Shilton | G21G 4/06 |
| 2003/0149329 | A1 | 8/2003 | O'Foghludha | |
| 2015/0102238 | A1 | 4/2015 | Finger et al. | |

FOREIGN PATENT DOCUMENTS

| | | |
|---|---|---|
| WO | PCT/US2017/03350 | 5/2017 |
| WO | PCT/US2017/050425 | 9/2017 |
| WO | 2019/246073 | 12/2019 |

OTHER PUBLICATIONS

International Search Report issued in PCT/US2020/017601 dated Jul. 17, 2020.

International Search Report issued in PCT/US2019/037697 dated Sep. 26, 2019.

V. Raghavan, "Al—B—Ir (Aluminum-Boron-Iridum)", Journal of Phase Equilibria and Diffusion, vol. 29, No. 1, 2008, p. 42.

V. Raghavan, "Al—Ir—V (Aluminum-Iridium-Vanadium)", Journal of Phase Equilibria and Diffusion, vol. 29, No. 4, 2008, p. 372.

H. Ipser and P. Rogl, "Constitution Diagrams of the Binary Systems Pd—B and Ir—B", Elsevier Sequoia/Printed in The Netherlands, Metall. Trans. A., 1981, p. 363.

G. B. Ulrich, "The Metallurgical Integrity of the Frit Vent Assembly Diffusion Bond", Process Metallurgy Department Development Organization, Jun. 1994, pp. 1-22.

himikatus.ru, http://www.himikatus.ru/art/phase-diagr1/Al-Ir.php, pp. 1-5.

* cited by examiner

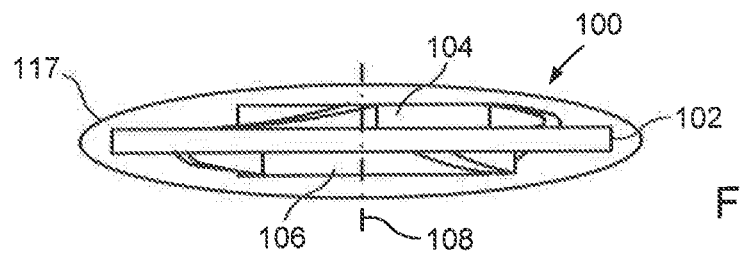
FIG. 4
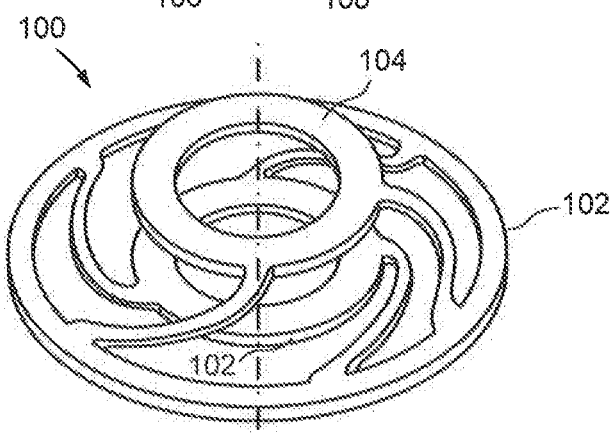
FIG. 3
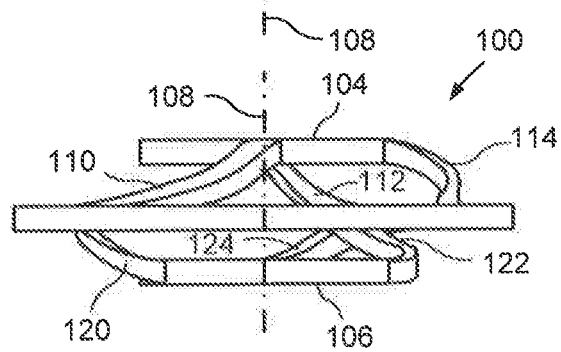
FIG. 2
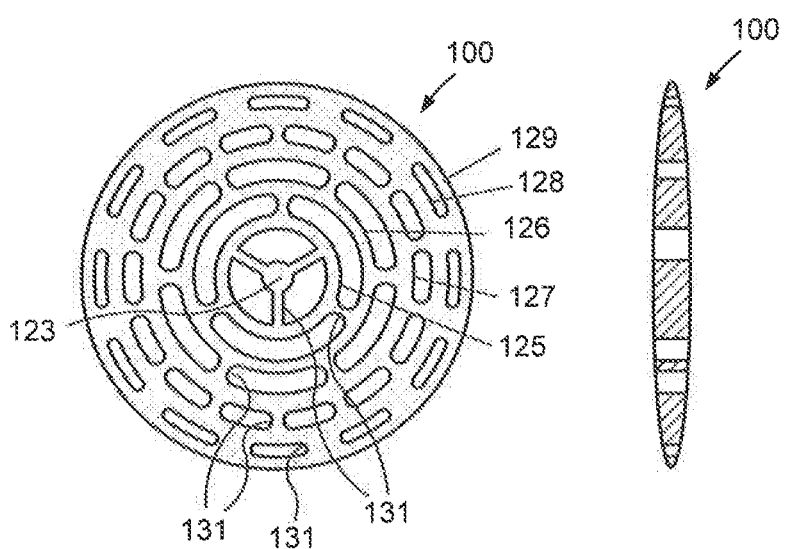 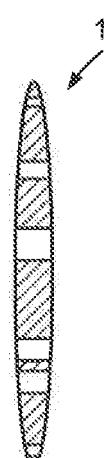
FIG. 5A   FIG. 5B

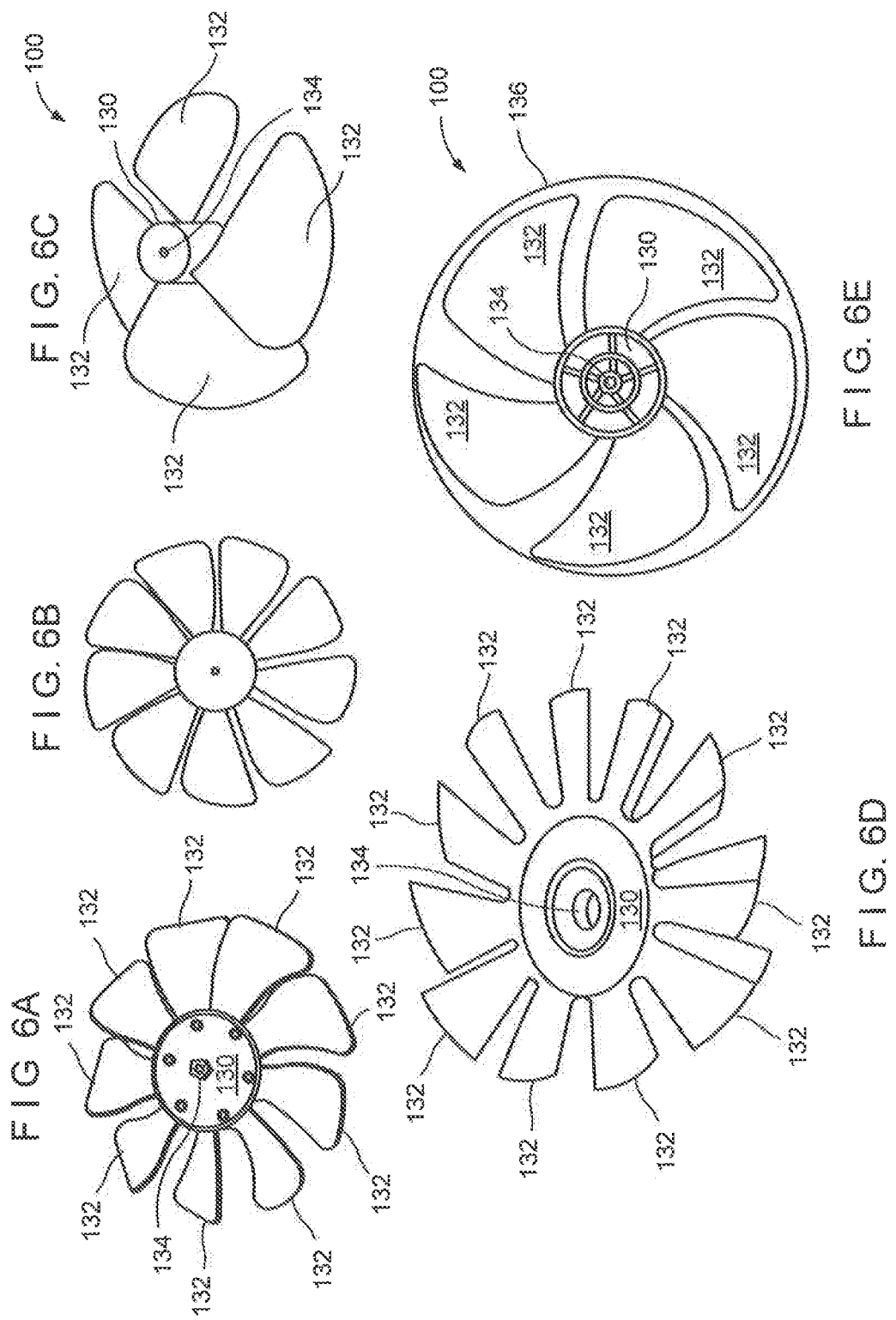

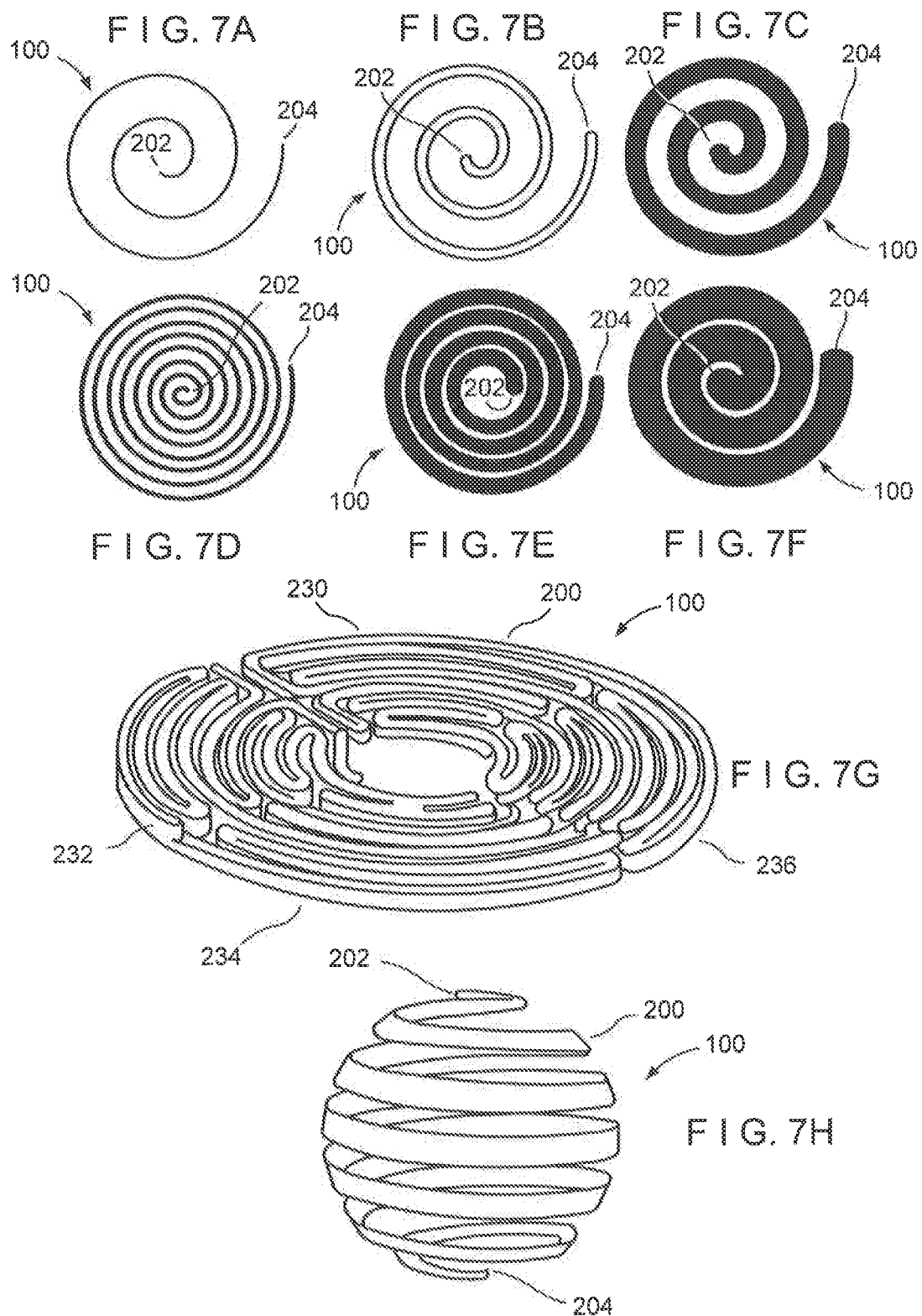

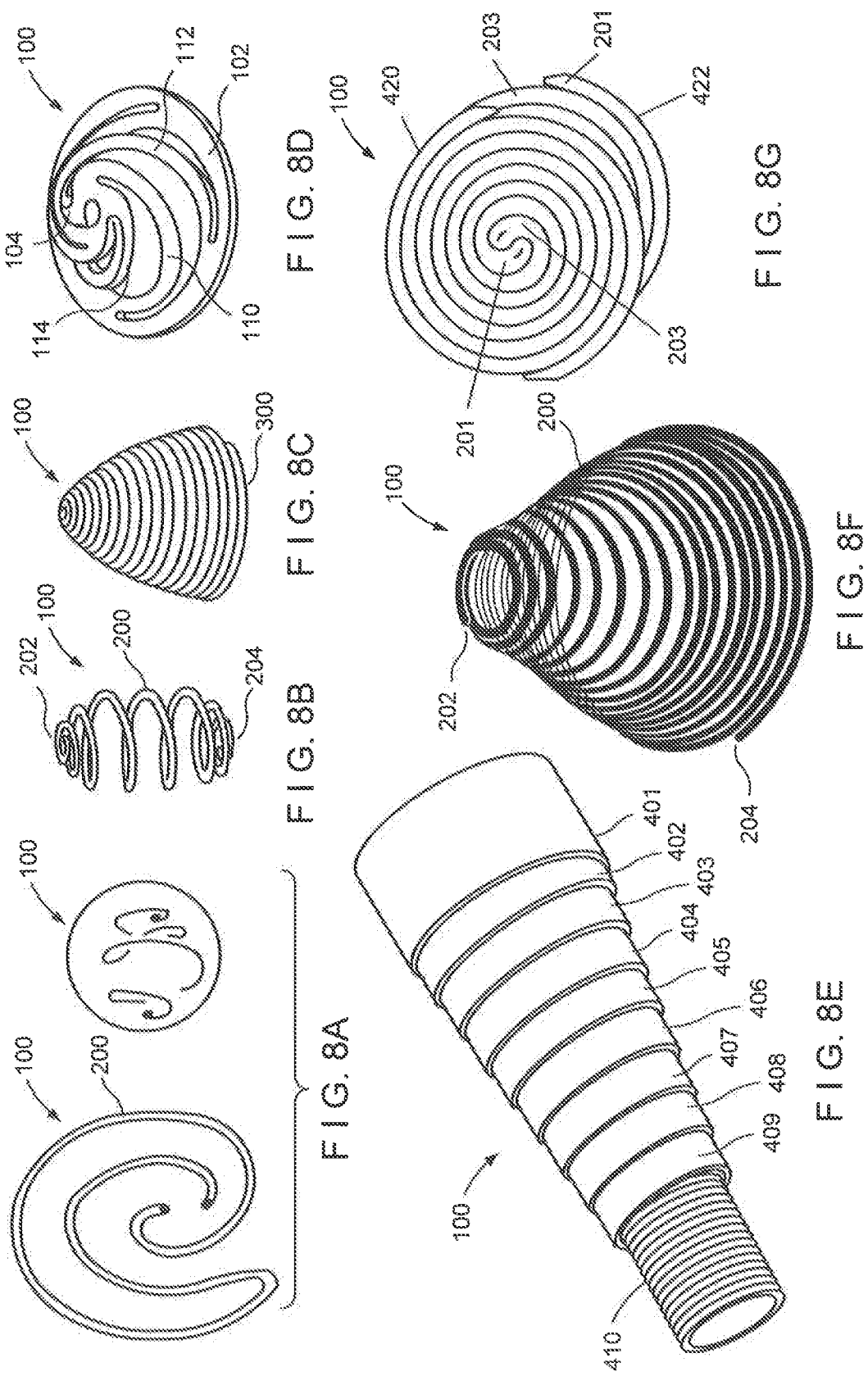

GAMMA RADIATION SOURCE COMPRISING LOW-DENSITY DEFORMABLE/COMPRESSIBLE IRIDIUM ALLOY AND AN ENCAPSULATION

This application claims priority under 35 U.S.C. 119(e) of U.S. provisional application Ser. No. 62/686,748, filed on Jun. 19, 2018, the contents of which is hereby incorporated by reference in its entirety and for all purposes.

BACKGROUND OF THE DISCLOSURE

Field of the Disclosure

The disclosure pertains to improvements in a gamma radiation source (including radiological and radiographic sources), typically containing low-density alloys or compounds or composites of iridium in mechanically deformable and compressible configurations, for use within a sealed encapsulation, and methods of manufacture thereof.

Description of the Prior Art

Improvements in iridium sources have been described in PCT/US2017/033508 entitled "Low Density Spherical Iridium"; PCT/US2017/050425 entitled "Low Density Porous Iridium"; and PCT/US2015/029806 entitled "Device and Method for Enhanced Iridium Gamma Irradiation Sources." The disclosures of these applications are well-suited to their intended purposes. However, further improvements and refinements are sought.

OBJECTS AND SUMMARY OF THE DISCLOSURE

It is therefore an object of this application to provide improvements and refinement with respect to the above-identified prior art.

Objects of this disclosure include:

1. developing a deformable and/or compressible low density iridium alloy containing 30-85% (volume percentage) Iridium, preferably in the range of 30-70%, more preferably in the range of 40-60%.

2. the alloying constituents ideally or typically should not irradiate to produce other radionuclides that generate interfering gamma rays.

3. the alloying constituents ideally or typically should not have excessively high density or high neutron activation cross-section, which could decrease the activation yield or decrease the source-output yield of Iridium-192.

4. the alloying constituents ideally or typically should produce an alloy that is workable in that the alloy needs to be sufficiently ductile/deformable/compressible whereas pure iridium and most of its alloys are brittle and unworkable; the alloy ideally or typically should preferably have a lower melting point than pure iridium (a melting point less than 2000 degrees Centigrade would be desirable to lower processing costs and simplify thermal technologies); and the alloy ideally or typically should be substantially physicochemically inert (i.e., it does not oxidize/corrode/decompose under conditions of manufacture or use).

The general class of compounds that are predicted to have suitable mechanical and density properties are called $L2_1$ Heusler structures. Specifically, these comprise $Ir_2M_1N_1$, where M and N represent two different metals. $Ir_2MnAl$ is described above. $Ir_2CrAl$ Is a potential alternative. There may be others, e.g., $Ir_2Al$ and $Ir_2Al^{11}B$.

With regard to the $L2_1$ Heusler compounds and structures, a range of compounds and structures should be taken into account. It is known that after irradiation of a $L2_1$ Heusler compound like $Ir_2MnAl$, it would transmute to $Ir_{2-(x+y)}Pt_xOs_yMnAl$ where "x+y" is the proportion of iridium that transmutes to platinum and osmium. There is typically approximately 10-20% conversion, depending on neutron flux, enrichment, irradiation time and decay time (burn-up/transmutation) in an irradiation. Iridium-191 (37.3% in natural iridium, approximately 80% in enriched iridium) activates to Iridium-192 of which approximately 95% decays to Platinum-192 and 5% decays to Osmium-192 over the life of the source. Iridium-193 (62.7% in natural iridium, ~20% in enriched iridium) activates to Iridium-194, which all decays to Platinum-194 in the reactor. In summary, an irradiated disk may contain roughly 5-20% platinum and 0.25-1% osmium after activation, depending on the flux, time and enrichment. It is the post-irradiated alloy that is desired to be ductile, deformable or compressible. The addition of platinum to iridium is likely to increase ductility.

Even if pre-irradiated alloy disks do not have optimum mechanical properties for source manufacture, post-irradiated disks may. Quaternary alloys that contain small amounts of other ingredients, such as, but not limited to, platinum or osmium, or other purposeful additions included before irradiation (such as, but not limited to, chromium) may improve the physicochemical and mechanical properties without activating adversely. Ternary and quaternary alloys are synthesized to account for the conversion of 10-20 atom % of the Iridium to its daughters platinum and osmium in the nuclear reactor. Representative alloys in this regard include $Ir_{1.8}Pt_{0.2}MnAl$ and $Ir_{1.6}Pt_{0.4}MnAl$, also including a very small percentage of osmium. A further representative alloy is $Ir_3Zr_{0.25}V_{0.75}$.

Similarly, yttrium alloyed with iridium has increased ductility. Stable, natural $^{89}$Yttrium activates with very low cross section to form a very small amount of radioactive $^{90}$Yttrium, a pure beta emitter with a 64 hour half-life. It is therefore an acceptable metal to co-irradiate with Iridium. It does not produce long term interfering gamma rays. Moreover, $^{90}Y$ decays to stable zirconium. Yttrium is therefore one of the preferred alloying additives. The most likely composition is IrY (i.e. 50/50-atomic percent alloy), but other ratios of $Ir_xY_y$ may also have increased ductility. Further representative alloys include IrY, $Ir_{0.9}Pt_{0.1}Y$, and $Ir_{0.8}Pt_{0.2}Y$.

The density of $Ir_2MnAl$ is reported or calculated to be 13.89 g/cc vs. 22.56 g/cc for pure iridium (i.e., 61.5%). Further studies may confirm or refine this number. This is slightly higher than optimum for many applications, therefore this alloy may be used for porous or 3-D printed shapes that contain empty spaces, so that the net density may be reduced to the optimum range of 30-85% (preferably in the range of 30-70%, more preferably 40-60%), as illustrated in the various figures of this application. It is also expected that these compounds may have anti-ferromagnetic properties.

These alloys may be formed by mixing powdered elements in molar proportions, e.g. $Ir_2+Mn+Al$ and heating—e.g. arc melting or using a high temperature vacuum furnace. As a variant of this basic method, it is expected, under some circumstances, to advantageously first pre-alloy Mn+Al and then mix/process this with pure iridium. MnAl melts at approximately 1500 degrees Centigrade.

Other approaches may include pre-alloying iridium and aluminum and then adding Mn or Mn+Al later. The alloy composition Al$_7$Ir$_3$ (i.e. 30 mol % Iridium) is reported to have a eutectic at approximately 1930 degrees Kelvin (1657 degrees Centigrade).

Reference is made to the article "Antiferromagnetism in γ-Phase Mn—Ir Alloys," as reported in the Journal of the Physical Society of Japan in 1974, pages 445-450 (Online ISSN: 1347-4073, Print ISSN 0031-9015). This article indicates that antiferromagnetic disordered γ-phase Mn$_{(1-x)}$Ir$_x$ (0.05<x<0.35) alloys exists. Mixing an Ir+Mn alloy in this composition range, e.g. Mn$_7$Ir$_{11}$ powder or granules with Al$_7$Ir$_3$ powder or granules in equimolecular proportions followed by thermal processing (arc melting or furnace) is expected to produce an alloy with a composition of Ir$_{14}$Mn$_7$Al$_7$ (=Ir$_2$MnAl).

BRIEF DESCRIPTION OF THE DRAWINGS

Further objects and advantages of the disclosure will become apparent from the following description and from the accompanying drawings, wherein:

FIG. 2 is a side view of the compressible disk of FIG. 1.

FIG. 3 is a perspective view of the compressible disk of FIG. 1.

FIG. 4 is a side view of the compressible disk of FIG. 1, after compression, within a sealed encapsulation.

FIGS. 5A and 5B are a front plan view and a side plan view of a further embodiment of the compressible disk of the present disclosure.

FIGS. 6A-6E are front plan views of fan-blade type embodiments of the present disclosure.

FIGS. 7A-7H disclose further embodiments of compressible disks of the present disclosure.

FIGS. 8A-8G disclose still further embodiments of compressible disks of the present disclosure.

DETAILED DESCRIPTION OF THE PREFERRED EMBODIMENTS

Figure 1:
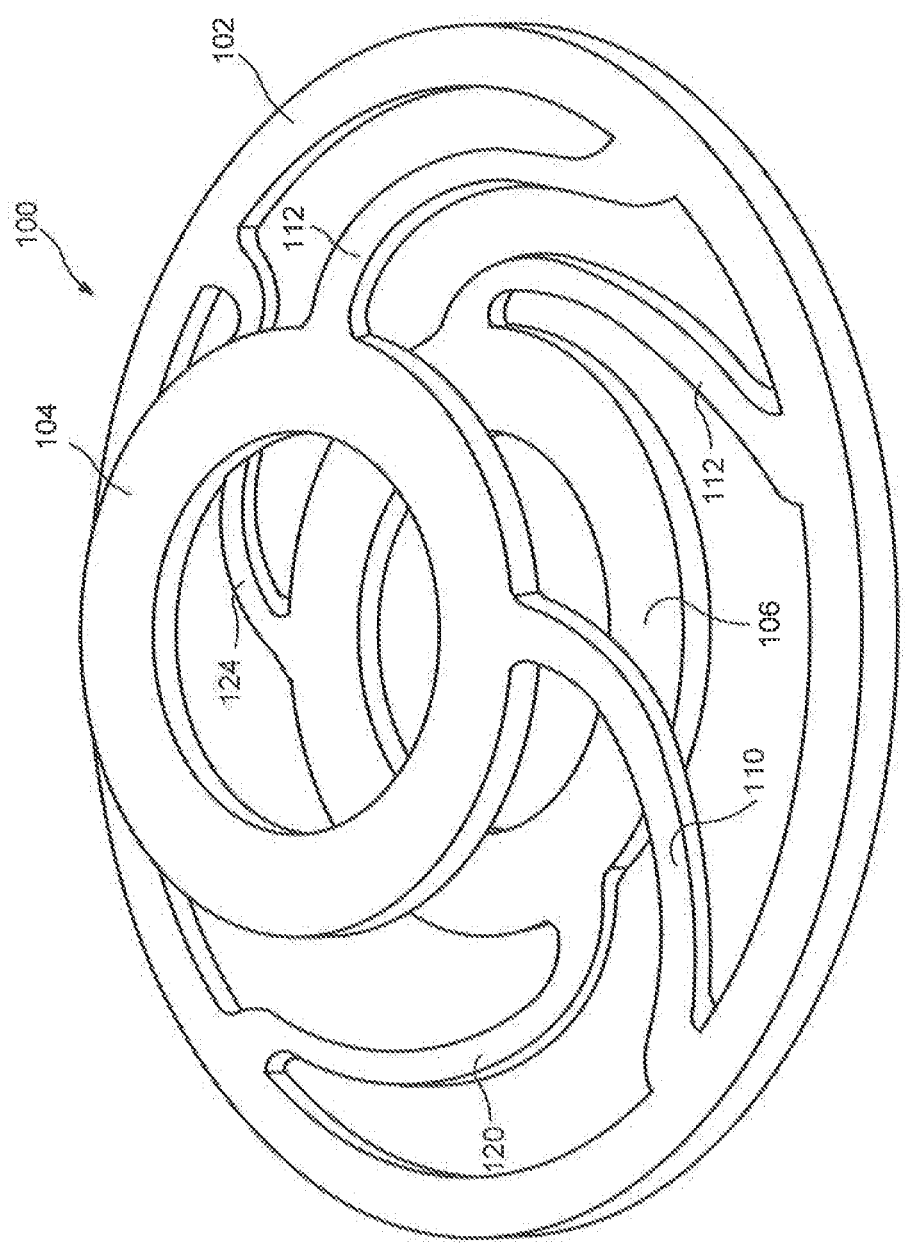
FIG. 1 is a perspective drawing of an embodiment of a deformable and compressible disk using a deformable compressible iridium alloy of the present disclosure.

In accordance with the above, the alloy Ir$_2$MnAl forms an embodiment of the present disclosure of a gamma radiation source (including radiological and radiographic sources). It is believed to have ductile properties similar to steel. Additionally, manganese and aluminum are not expected to generate interfering gamma rays after activation by neutron irradiation. Platinum, osmium, chromium or mixtures thereof may likewise be found within the alloy.

This alloy or similar alloys (such as with ternary additions of other non-activating elements) is expected have suitable mechanical properties to make deformable/compressible radiation sources. Although the addition of manganese slightly increases the density with respect to iridium plus aluminum or iridium plus aluminum plus Boron-11, it is expected that the metallurgical properties of Ir$_2$MnAl may offer significant processing advantages.

Iridium manganese copper alloys are also applicable to the present disclosure. These alloys are expected to be ductile and have a melting point significantly below 2000 degrees Centigrade and potentially as low as 1300 degrees Centigrade, depending upon the alloy composition after irradiation. These alloys are disclosed in U.S. Pat. No. 4,406,693 entitled "Method for Refining Contaminated Iridium," issued on Sep. 27, 1983. However, it is expected that aluminum will be preferable over copper as a tertiary alloying element in most applications.

Yttrium alloyed with indium is likewise a relevant material for the present disclosure.

Furthermore, reduced density may be achieved in some embodiments by the use of porous, microporous or macroporous (i.e., metal foam) forms of the alloy of choice.

All radiation sources are typically designed and expected to be inserted into a sealed encapsulation.

Referring now to FIGS. 1 through 4, one sees illustrations of an embodiment of a deformable/compressible non-solid shape for a gamma radiation source 100 (which may be a radiological or radiographic source) that may be made using a deformable/compressible iridium alloy. Gamma radiation source 100 may be manufactured by 3-D printing but is not limited thereto. Further, gamma radiation source 100, as well as all embodiments disclosed herein, are implemented within a sealed encapsulation. Gamma radiation source 100 of FIGS. 1-4 includes a central ring or disk 102, along with an upper ring or disk 104 and a lower ring or disk 106 of somewhat reduced diameter. Rings 102, 104, 106 generally share a common rotational axis 108, as shown in FIGS. 2-4, and are generally parallel to each other in an uncompressed or uniformly compressed configuration. Upper ring 104 is positioned above the central ring 102 by arms 110, 112, 114 spiraling rotationally outwardly from an exterior circumferential surface of upper ring 104 to an interior circumferential surface of central ring 102. Similarly, lower ring 106 is positioned below the central ring 102 by arms 120, 122, 124 spiraling rotationally outwardly from an exterior circumferential surface of lower ring 106 to an interior circumferential surface of central ring 102. The elasticity and flexibility of spiraling arms 110, 112, 114, 120, 122, 124 allows for forces generally parallel with the common rotational axis 108 to compress the gamma radiation source 100 from the configuration shown in FIGS. 1 and 2 to the configuration shown in FIG. 4. Furthermore, in the compressed configuration of FIG. 4, gamma radiation source 100 is sealed within an encapsulation 117. Those skilled in the art will recognize that different shapes and configurations of encapsulation may be used for different applications, and that shapes different from that of the illustrated encapsulation may be used.

FIGS. 5A and 5B illustrate an embodiment of gamma radiation source 100 wherein concentric co-planar rings 125, 126, 127, 128, 129 of deformable/compressible iridium alloy area positioned around a center 123, with radial structural spoke segments 131 extending from center 123 to innermost ring 125, and then between successively or sequentially concentrically adjacent rings, 125, 126; 126, 127; 127, 128; and 128, 129. FIG. 5B illustrates the elongated shape of the side view of gamma radiation source 100. The resulting configuration can be folded and/or compressed into different shapes to achieve an increased average density. This gamma radiation source 100 is made from a deformable/compressible iridium alloy, may be made by 3-D printing, and is sealed within an encapsulation (see FIG. 4, element 117).

FIG. 6A-6E illustrate embodiments of the gamma radiation source 100 which include a central cylindrical shaft-type hub area 130 with a rotational axis 134 at the center and with propeller-type radial extensions 132 extending therefrom. Additionally. FIG. 6F includes an outer circular ring 136 joining the distal ends of the propeller-type radial extensions 132. These propeller type radial extensions 132, in the illustrated uncompressed slates, are oriented at an angle analogous to the pitch or blade angle of a conventional propeller. While different applications may use different angles, a typical pitch or propeller angle may be in the range of 30 to 60 degrees. However, as a result of forces of compression generally parallel to the rotational axis 134, the propeller angle of the propeller-type radial extensions 132 reduces so that the angle between the planar surface of the central cylindrical shaft-type hub area 130 and the propeller-type radial extensions 132 reduces so that the propeller-type radial extensions 132 approach a planar configuration with the central cylindrical shaft-type hub area 130. This decreases the volume which generally envelopes the gamma radiation source 100, thereby increasing the average density within the volume. These gamma radiation sources 100 are made from a deformable/compressible iridium alloy, may be made by 3-D printing, and are sealed within an encapsulation (see FIG. 4, element 117).

FIGS. 7A-7F illustrate spiral configurations of the gamma radiation source 100 comprising a rod, tube or other extended configuration 200 of deformable iridium alloy, or similar material. Rod, tube or other extended configuration 200 includes a first end 202 and a second end 204. The spiral configuration places first end 202 at an interior location in the spiral and the second end 204 at an exterior location in the spiral. The spiral configuration, along with the deformable, and possibly elastic, property of the rod, tube or other extended configuration 200 allows the spiral to be tightened so as to occupy less volume, and therefore have a higher average density. In many applications, these shapes are adaptable to 3-D printing.

FIG. 7G illustrates an embodiment of gamma radiation source 100 wherein a rod, tube or other extended configuration 200 of deformable iridium alloy or similar material is successively looped and placed at increasing radial locations, within each of four quadrants 230, 232, 234, 236. As shown in FIG. 7G, alternate loops may extend between two adjacent quadrants. The resulting structure can be stretched or compressed within the plane of gamma radiation source 100 or folded upon itself to alter the average density of the gamma radiation source 100. In many applications, this shape is adaptable to 3-D printing.

FIG. 7H illustrates an embodiment of gamma radiation source 100 wherein a rod, tube or other extended configuration 200 of deformable iridium alloy or similar material is wrapped in a three-dimensional spiral shape so as to form a quasi-spherical shape in that the rod, tube or other extended configuration 200 covers a first portion of a quasi-spherical shape and a second portion of a quasi-spherical shape is left open, with ends 202, 204 generally at opposite poles of the quasi-spherical shape. The resulting three-dimensional spiral shape of the gamma radiation source 100 can be twisted or otherwise compressed into a configuration of increased average density. In many applications, this shape is adaptable to 3-D printing.

FIGS. 8A-8G illustrate further embodiments of the gamma radiation source 100 of the present disclosure. FIG. 8A illustrates how a rod, tube or other extended configuration 200 of deformable iridium alloy or similar material may be wrapped or looped within a single plane. This gamma radiation source 100 may be twisted or compressed into a configuration of increased average density. In many applications, this shape is adapted to 3-D printing.

FIG. 8B illustrates an embodiment of a gamma radiation source 100 similar to that of FIG. 7H. A rod, tube or other extended configuration 200 of deformable iridium alloy or similar material is wrapped in a three-dimensional spiral shape so as to form a quasi-ellipsoidal shape in that the rod, tube or other extended configuration 200 covers a first portion of a quasi-ellipsoidal shape and a second portion of a quasi-ellipsoidal shape is left open, with ends 202, 204 generally at opposite poles of the quasi-ellipsoidal shape. The resulting three-dimensional spiral shape of the gamma radiation source 100 can be twisted or otherwise compressed into a configuration of increased average density. In many applications, this shape is adaptable to 3-D printing.

FIG. 8C illustrates an embodiment of the gamma radiation source 100 wherein a ribbon-like configuration 300 of deformable iridium alloy or similar material is wrapped in a three-dimensional projectile or nosecone-type shape. This shape may be pushed downward to form a tightly wrapped spiral configuration of increased average density. In many applications, this shape is adaptable to 3-D printing.

FIG. 8D illustrates an embodiment of gamma radiation source 100 similar to that of FIGS. 1-4. In FIG. 8D, a relatively larger ring 102 is provided with, along with a relatively smaller ring 104 in an upward position. Rings 102, 104 generally share a common rotational axis 108. Ring 104 is positioned above the ring 102 by arms 110, 112, 114 spiraling outwardly from an exterior circumferential surface of ring 104 to an interior circumferential surface of ring 102. The elasticity and flexibility of arms 110, 112, 114 allows for forces generally parallel with the rotational axis to compress the gamma radiation source 100. In many applications, this shape is adaptable to 3-D printing.

FIG. 8E illustrates an embodiment of gamma radiation source 100 which includes a series of interlocking sleeves 401-409 which are slidably engaged with inwardly or outwardly adjacent interlock sleeves. Interlocking sleeves 401-409, which are formed of a deformable iridium alloy or similar material may also be implemented as a spiral configuration of a single sheet of material. A spiral wire configuration 410 of similar material is engaged within an inner diameter of interlocking sleeve 409. This gamma radiation source 100 can be compressed to a reduced volume, thereby resulting in higher average density. In many applications, this shape is adaptable to 3-D printing.

FIG. 8F illustrates an embodiment of gamma radiation source 100 which is somewhat similar to that of FIGS. 7H and 8B in that a rod, tube or other extended configuration 200 of deformable iridium alloy or similar material is wrapped in a three-dimensional spiral shape so as to form a quasi-conical shape (with an open circular base) in that the rod, tube or other extended configuration 200 covers a first portion of the walls of a quasi-conical shape and a second portion of the walls of the quasi-conical shape is left open. The resulting three-dimensional spiral quasi-conical shape of the gamma radiation source 100 can be twisted or otherwise compressed into a configuration of increased average density. In many applications, this shape is adaptable to 3-D printing.

FIG. 8G illustrates an embodiment of gamma radiation source 100 wherein two adjacent disks 420, 422 each include first and second rods, tubes or other extended configurations 201, 203 of deformable iridium alloy or similar material are wrapped in a concentric spiral pattern. In the illustrated configuration, the first and second rods 201, 203 are wrapped in a clockwise configuration in first disk 420 and counterclockwise in second disk 422. The disks 420, 422 may be varied in relationship to each other, folded or otherwise compressed to vary the average density thereof. In many applications, this shape is adaptable to 3-D printing.

Thus the several aforementioned objects and advantages are most effectively attained. Although preferred embodiments of the invention have been disclosed and described in detail herein, it should be understood that this invention is in no sense limited thereby.

What is claimed is:

1. A radiation, radiological, or radiographic source including:
   a mechanically depressible, compressible non-solid configuration of:
      an alloy or a mixture of iridium, manganese, and an element chosen from a group consisting of aluminum, copper, and mixtures thereof, or
      an alloy or a mixture of iridium and yttrium.

2. The radiation, radiological, or radiographic source of claim 1, wherein the alloy or the mixture comprises Ir2MnAl.

3. The radiation, radiological, or radiographic source of claim 1, wherein at least a portion of iridium comprises Iridium-192.

4. The radiation, radiological, or radiographic source of claim 1, wherein the alloy or the mixture further includes an element chosen from the group consisting of platinum, osmium, chromium, or mixtures thereof.

5. The radiation, radiological, or radiographic source of claim 1, further including:
   at least a first element and a second element; and
   a mechanically-compressible portion between the first element and the second element, whereby a force on the first element causes the first element to move toward the second element.

6. The radiation, radiological, or radiographic source of claim 1, further including:
   at least a first element, a second element, and a third element;
   a first mechanically-compressible portion between the first element and the second element; and
   a second mechanically-compressible portion between the second element and the third element.

7. The radiation, radiological, or radiographic source of claim 6, wherein the first element comprises a first ring or disk, the second element comprises a second ring or disk, and the third element comprises a third ring or disk, and wherein the second ring or disk is positioned between the first ring or disk and the third ring or disk.

8. The radiation, radiological, or radiographic source of claim 7, wherein the first ring or disk, the second ring or disk, and the third ring or disk are coaxial.

9. The radiation, radiological, or radiographic source of claim 8, wherein the first ring or disk, the second ring or disk, and the third ring or disk are parallel to each other in an uncompressed or uniformly-compressed configuration.

10. The radiation, radiological, or radiographic source of claim 8, wherein a radius of the second ring or disk is greater than a radius of the first ring or disk and a radius of the third ring or disk.

11. The radiation, radiological, or radiographic source of claim 8, wherein the first mechanically-compressible portion and the second mechanically-compressible portion include a plurality of rotationally-spiraling arms.

12. The radiation, radiological, or radiographic source of claim 11, wherein the rotationally-spiraling arms spiral outwardly from the first ring or disk and the third ring or disk to the second ring or disk.

13. The radiation, radiological, or radiographic source of claim 1, further including:
    a plurality of co-planar and co-axial rings; and
    a plurality of radial spoke segments joining sequential rings of the plurality of co-planar and co-axial rings.

14. The radiation, radiological, or radiographic source of claim 1, further including:
    a central hub and propeller-type assemblies extending radially therefrom.

15. The radiation, radiological, or radiographic source of claim 14, wherein the propeller-type assemblies are configured with respect to the central hub to form a pitch angle.

16. The radiation, radiological, or radiographic source of claim 15, wherein the pitch angle is in the range of 30 to 60 degrees.

17. The radiation, radiological, or radiographic source of claim 16, wherein; under a compression, the propeller-type assemblies are urged toward a configuration planar with the central hub.

18. The radiation, radiological, or radiographic source of claim 1, wherein a planar spiral configuration is formed.

19. The radiation, radiological, or radiographic source of claim 1, wherein a three-dimensional spiral configuration is formed.

20. The radiation, radiological, or radiographic source of claim 19, wherein the three-dimensional spiral configuration is substantially spherical or ellipsoidal.

* * * * *